United States Patent [19]

Kando et al.

[11] Patent Number: 5,696,256
[45] Date of Patent: Dec. 9, 1997

[54] PROCESS FOR PREPARING AND USING GUANIDINE DERIVATIVES

[75] Inventors: Yasuyuki Kando; Hideki Uneme; Isao Minamida, all of Tsukuba, Japan

[73] Assignee: Takeda Chemical Industries, Ltd., Osaka, Japan

[21] Appl. No.: 439,790

[22] Filed: May 12, 1995

Related U.S. Application Data

[62] Division of Ser. No. 682,247, Apr. 9, 1991.

[30] Foreign Application Priority Data

Apr. 13, 1990 [JP] Japan ................... 2-098627
Aug. 17, 1990 [JP] Japan ................... 2-217356

[51] Int. Cl.$^6$ ............ C07D 211/44; C07D 207/12; C07D 205/04; C07D 223/10
[52] U.S. Cl. ............ 540/463; 548/952; 548/546; 546/243; 540/356; 540/526
[58] Field of Search ............ 540/356, 529, 540/463, 526; 546/243, 245; 548/545, 547, 548, 952

[56] References Cited

U.S. PATENT DOCUMENTS

| 4,287,346 | 9/1981 | Tanaka et al. ............ 546/330 |
| 4,742,060 | 5/1988 | Shiokawa et al. ............ 514/252 |
| 4,845,106 | 7/1989 | Shiokawa et al. ............ 514/342 |

FOREIGN PATENT DOCUMENTS

| 0232521 | 12/1985 | Australia ............ 540/356 |
| 0 260 560 | 3/1988 | European Pat. Off. . |
| 0 302 389 | 2/1989 | European Pat. Off. . |
| 0 366 085 | 10/1989 | European Pat. Off. . |
| 0 375 907 | 11/1989 | European Pat. Off. . |
| 0 376 279 | 12/1989 | European Pat. Off. . |
| 0 381 130 | 1/1990 | European Pat. Off. . |
| 0 391 205 | 3/1990 | European Pat. Off. . |
| 225129 | 7/1985 | German Dem. Rep. . |
| 0217043 | 9/1961 | Germany ............ 540/356 |

OTHER PUBLICATIONS

Chemical Abstracts, vol. 89(17):146820b (1978).
Chupp et al., J. Org. Chem., 43(18), 3553–59, 1978.
G.J. Durant et al., "Cyanoguanidine—Thiourea Equivalence in the Development of the Histamine H2-Receptor Antagonist, Cimetidine," Journal of Medicinal Chemistry, vol. 20, No. 7, (1977), pp. 901–906.

*Primary Examiner*—John M. Ford
*Attorney, Agent, or Firm*—Foley & Lardner

[57] ABSTRACT

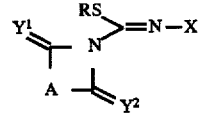

wherein R is a substituted or unsubstituted hydrocarbon residue or acyl group; X is an electron withdrawing group; $Y^1$ and $Y^2$, which are the same or different, are each independently oxygen or sulfur; and A is a substituted or unsubstituted, divalent hydrocarbon residue have potent reactivity, this being useful in preparing guanidine derivatives.

2 Claims, No Drawings

PROCESS FOR PREPARING AND USING GUANIDINE DERIVATIVES

This application is a division, of application Ser. No. 07/682,247, filed Apr. 9, 1991.

FIELD OF THE INVENTION

The present invention relates to a process for preparing guanidine derivatives, intermediates for the preparation of the said guanidine derivatives, and a process for preparing the said intermediates. The said guanidine derivatives are useful as insecticides and miticides (see Japanese Patent Application No.333721/1989).

BACKGROUND OF THE INVENTION

Heretofore, as a process for preparing N-substituted-N'-nitroisothiourea derivatives and N-cyclic(methyl)-N'-nitroisothiourea derivatives, which are useful as intermediates for the preparation of guanidine derivatives, there has been known a nitration process using sulfuric acid-fuming nitric acid for isothioureas [see "Journal of American Chemical Society," Vol. 76, p.1877, (1954)]. According to this known process, however, the yield in the nitration of isothioureas which have alkyl substituents on the nitrogen is extremely low and so this process has not been satisfactory as a general synthesis process or an industrial manufacturing process.

SUMMARY OF THE INVENTION

The present invention has been accomplished in view of the above-mentioned circumstances and it is the object thereof to find out novel synthetic intermediates for the preparation of N,N'-disubstituted isothiourea derivatives and N-cyclic (methyl)-N'-substituted isothiourea derivatives which are both useful as synthetic intermediates to guanidine derivatives, using a technique capable of being practiced industrially and economically in high yield, and to provide a process for preparing the said intermediates, as well as a process for preparing novel guanidine derivatives which are extremely useful as insecticides and miticides, using the said intermediates.

Having made extensive studies for attaining the above-mentioned subject, the present inventors found out that compounds represented by the following formula I

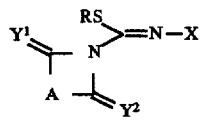  [I]

wherein R is a substituted or unsubstituted hydrocarbon radical or acyl group; X is an electron withdrawing group; $Y^1$ and $Y^2$, which are the same or different, are each independently oxygen or sulfur; and A is a substituted or unsubstituted divalent hydrocarbon residue, are highly reactive unexpectedly and that in these compounds the cyclic di(thio)acylimide moiety is preferentially substituted by amines, followed by a substitution reaction of the RS moiety:

As a result of these studies, we have now completed the present invention.

The present invention relates to (1) a compound of the formula [I]

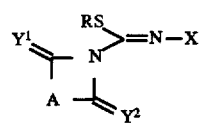  [I]

wherein R is a substituted or unsubstituted hydrocarbon radical or acyl group; X is an electron withdrawing group; $Y^1$ and $Y^2$, which are the same or different, are each independently oxygen or sulfur; and A is a substituted or unsubstituted, divalent hydrocarbon residue;

(2) a process for preparing a compound of the formula [I], which comprises reacting a compound of the formula

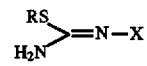  [II]

wherein R and X are as defined previously, with a compound of the formula

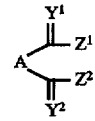  [III]

wherein A, $Y^1$ and $Y^2$ are as defined previously, $Z^1$ and $Z^2$, which are the same or different, are each independently halogen or $Z^1$ and $Z^2$ taken together represent oxygen;

(3) a process for preparing a compound of the following formula or a salt thereof:

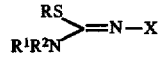  [V]

wherein R and X are as defined previously, $R^1$ and $R^2$, which are the same or different, are each independently hydrogen or a substituted or unsubstituted hydrocarbon residue or taken together with the vicinal nitrogen form a cyclic amino group, which comprises reacting a compound of the formula [I] with an amine of the following formula or a salt thereof:

  [IV]

wherein $R^1$ and $R^2$ are as defined above;

(4) a process for preparing a compound of the following formula or a salt thereof:

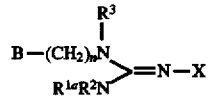  [VIII]

wherein B is a substituted or unsubstituted, homocyclic or heterocyclic group; n is 0 or 1; $R^3$ is hydrogen or a substituted or unsubstituted hydrocarbon residue, and $R^{1a}$ is a hydrogen atom, a substituted or unsubstituted hydrocarbon residue or acyl group, $R^2$ and X are as defined above, which comprises reacting the compound of the formula [V] or salt thereof prepared by the process of step 3 with a compound of the following formula or a salt thereof after acylation if necessary when $R^1$ represents a hydrogen atom:

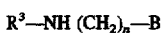  [VI]

wherein $R^3$, n and B are as defined above;

(5) a process for preparing a compound of the following formula or a salt thereof:

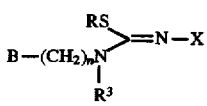

[VII]

wherein B, R, R³, n and X are as defined above, which comprises reacting a compound of the formula [I] with a compound of the following formula or a salt thereof:

$$R^3-NH(CH_2)_n-B \quad [VIII]$$

wherein R³, n and B are as defined above; and (6) a process for preparing a compound of the following formula or a salt thereof:

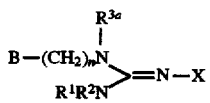

[IX]

wherein B, n, R¹, R² and X are as defined above, and R³ᵃ is a hydrogen atom or a substituted or unsubstituted hydrocarbon residue or acyl group, which comprises reacting the compound [VII] or salt thereof prepared by the process (5) with an amine of the following formula or a salt thereof after acylation if necessary when R³ represents a hydrogen atom:

$$R^1R^2NH$$

wherein R¹ and R² are as defined above.

The intermediate compounds [I] according to the present invention are excellently reactive and advantageously selective, thereby being useful in the preparation of valuable guanidine insecticides and miticides.

DETAILED DESCRIPTION OF THE INVENTION

According to the present invention, there are provided novel compounds of the formula [I] and novel processes for preparing compounds of the formulas IV], [VII], [VIII], and [IX] by use of the compound [I].

Further, the present invention provides processes for producing the compound [I] which is of value in the preparation of insecticidal and miticidal guanidine derivatives.

As examples of the substituted or unsubstituted hydrocarbon residue or acyl group as substituent R in the above formulae there are mentioned $C_{1-10}$ alkyl groups, $C_{2-10}$ alkenyl groups, $C_{2-10}$ alkynyl groups, $C_{7-12}$ aralkyl groups, and $C_{1-10}$ acyl groups, all of which may be substituted. Said $C_{1-10}$ acyl group may be aliphatic, alicyclic, aromatic, or heterocyclic as mentioned herein below. Examples of $C_{1-10}$ alkyl groups in the substituent R include straight-chain alkyl groups such as methyl, ethyl, n-propyl, n-butyl, n-pentyl, n-hexyl, n-heptyl, n-octyl, and n-decyl; branched alkyl groups such as i-propyl, i-butyl, s-butyl, t-butyl, i-pentyl, s-pentyl, t-pentyl, i-hexyl, s-hexyl, and t-hexyl; and cyclic alkyl groups such as cyclopropyl, cyclobutyl, cyclopentyl, cyclohexyl, and cycloheptyl. Examples of $C_{2-10}$ alkenyl groups for R include vinyl, allyl, 2-butenyl, and 1-pentenyl. Examples of $C_{2-10}$ alkynyl groups for R include 1-ethynyl, propargyl, 2-butynyl, and 1-pentynyl. Examples of $C_{1-10}$ acyl groups for R include straight-chain $C_{1-10}$ acyl groups such as formyl, acetyl, and propionyl, as well as acyl groups obtained by substituting the valence-side end methylene group in each of the alkyl groups exemplified above as $C_{1-10}$ alkyl groups with carbonyl group. Examples of $C_{7-12}$ aralkyl groups for R include benzyl, 1-phenethyl, 2-phenethyl, 1-naphthylmethyl, and 2-naphthylmethyl. These $C_{1-10}$ alkyl, $C_{2-10}$ alkenyl, $C_{2-10}$ alkynyl, $C_{1-10}$ acyl and $C_{7-12}$ aralkyl groups for R may each contain one to five same or different substituent groups. As examples of such substituent groups there are mentioned $C_{3-10}$ cycloalkyl groups such as cyclopropyl, cyclobutyl, cyclopentyl, and cyclohexyl; $C_{2-10}$ alkenyl groups such as vinyl, allyl, 2-methylallyl, 2-butenyl, 3-butenyl, and 3-octenyl; $C_{2-10}$ alkynyl groups such as ethynyl, 2-propynyl, and 3-hexynyl; $C_{3-10}$ cycloalkenyl groups such as cyclopropenyl, cyclopentenyl, and cyclohexenyl; nitro, hydroxyl, mercapto, oxo, thioxo, cyano, carbamoyl, carboxyl; $C_{1-4}$ alkoxycarbonyls such as methoxycarbonyl and ethoxycarbonyl; sulfo; halogens such as fluorine, chlorine, bromine and iodine; $C_{1-4}$ alkoxy groups such as methoxy, ethoxy, propoxy, isopropoxy, butoxy, isobutoxy, s-butoxy, and t-butoxy; $C_{6-10}$ aryloxy groups such as phenoxy; $C_{1-4}$ alkylthio groups such as methylthio, ethylthio, n-propylthio, isopropylthio, n-butylthio, and t-butylthio; $C_{6-10}$ arylthio groups such as phenylthio; $C_{1-4}$ alkylsulfinyl groups such as methylsulfinyl and ethylsulfinyl; $C_{6-10}$ arylsulfinyl groups such as phenylsulfinyl; $C_{1-4}$ alkylsulfonyl groups such as methylsulfonyl and ethylsulfonyl; $C_{2-6}$ arylsulfonyl groups such as phenylsulfonyl; amino; $C_{2-6}$ acylamino groups such as acetylamino and propionylamino; mono- or di-$C_{1-4}$ alkylamino groups such as methylamino, ethylamino, n-propylamino, isopropylamino, n-butylamino, dimethylamino, and diethylamino; $C_{3-6}$ cycloalkylamino groups such as cyclohexylamino; $C_{6-10}$ arylamino groups such as anilino; $C_{2-4}$ acyl such as acetyl; $C_{6-10}$ arylcarbonyl such as benzoyl; as well as five- to six-membered heterocyclic groups each containing ] to 4 hetero atoms selected from oxygen, sulfur and nitrogen, such as 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidinyl, 3- or 4-pyridazinyl, quinolyl, isoquinolyl, and indolyl. In the case where R is a substituted $C_{7-2}$ aralkyl or a substituted $C_{1-10}$ acyl, there are mentioned, as examples of the substituent group, $C_{1-15}$ alkyl groups such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, and pentadecyl; $C_{6-10}$ aryl groups such as phenyl and naphthyl; and $C_{7-10}$ aralkyl groups such as benzyl and phenylethyl. In the case where these substituent groups are, for example, $C_{6-10}$ aryl, $C_{7-10}$ aralkyl, $C_{3-10}$ cycloalkyl, $C_{3-10}$ cycloalkenyl, $C_{6-10}$ aryloxy, $C_{8-10}$ arylthio, $C_{6-10}$ arylsulfinyl, $C_{6-10}$ arylsulfonyl, $C_{6-10}$ arylamino, or heterocyclic groups, there may be further contained 1 to 5 substituents, examples of which include halogens such as those exemplified above, hydroxyl, $C_{1-4}$ alkyl groups such as methyl, ethyl, propyl, isopropyl, butyl, isobutyl, s-butyl, and t-butyl; $C_{2-4}$ alkenyl groups such as vinyl, allyl, and 2-methylallyl; $C_{2-4}$ alkynyl groups such as ethynyl and 2-propynyl; $C_{6-10}$ aryl groups such as those exemplified above; $C_{1-4}$ alkoxy groups such as those exemplified above; phenoxy; $C_{1-4}$ alkylthio groups such as those exemplified above; and phenylthio. In the case where the substituent groups are $C_{1-15}$ alkyl, $C_{2-10}$ alkenyl, $C_{2-10}$ alkynyl, $C_{1-4}$ alkoxy, $C_{1-4}$ alkylthio, $C_{1-4}$ alkylsulfinyl, $C_{1-4}$ alkylsulfonyl, amino, mono- or di-$C_{1-4}$ alkylamino, $C_{3-6}$ cycloalkylamino, or $C_{6-10}$ arylamino, there may be further contained 1 to 5 substituents, examples of which include halogens such as those exemplified above, hydroxyl, $C_{1-4}$ alkoxy groups such as methoxy and ethoxy, and $C_{1-4}$ alkylthio groups such as methylthio and ethylthio.

Preferred examples of R are $C_{1-4}$ alkyl groups such as methyl and ethyl and $C_{7-10}$ aralkyl groups such as benzyl.

As examples of the substituted or unsubstituted, divalent hydrocarbon residue as A in the foregoing formulae there are mentioned substituted or unsubstituted, saturated or unsaturated, divalent, acyclic hydrocarbon residues having 1 to 4 carbon atoms, and substituted or unsubstituted, saturated or unsaturated, divalent, cyclic hydrocarbon residues having 3 to 8 carbon atoms.

Examples of the said acyclic hydrocarbon residues include substituted or unsubstituted, divalent, $C_{1-4}$ alkylene or $C_{2-4}$ alkenylene groups. Examples of the above cyclic hydrocarbon residues include hydrocarbon residues represented by the following formula:

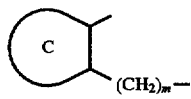

wherein the C-ring represents a substituted or unsubstituted, saturated or unsaturated, cyclic $C_{3-8}$ hydrocarbon, and m is 0 or 1.

Examples of the C-ring include substituted or unsubstituted benzene rings, $C_{3-8}$ cycloalkanes, and $C_{3-8}$ cycloalkenes.

In the foregoing "substituted or unsubstituted, divalent $C_{1-4}$ alkylene groups," as examples of divalent $C_{1-4}$ alkylene groups there are mentioned —$CH_2$—, —$CH_2CH_2$—,

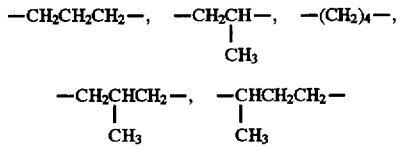

In the foregoing "substituted or unsubstituted, divalent $C_{2-4}$ alkenylene groups," as examples of divalent $C_{2-4}$ alkenylene groups there are mentioned —CH=CH—,

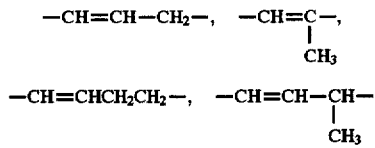

In the "substituted or unsubstituted $C_{3-8}$ cycloalkanes and $C_{3-8}$ cycloalkenes" of the C-ring, as examples of $C_{3-8}$ cycloalkanes and $C_{3-8}$ cycloalkenes there are mentioned cyclopropane, cyclobutane, cyclopentane, cyclohexane, cycloheptane, cyclooctane, cyclopentene, and cyclohexene.

The acyclic or cyclic hydrocarbon radicals exemplified above as A in the foregoing formulae may each contain 1 to 5 substituent groups. As examples of such substituent groups there are mentioned halogens such as fluorine, chlorine, bromine, and iodine; $C_{1-4}$ alkyl groups such as methyl, ethyl, n-propyl, i-propyl, n-butyl, s-butyl, and t-butyl; $C_{1-4}$ alkoxy groups such as methoxy, ethoxy, n-propoxy, n-butoxy, and t-butoxy; $C_{1-5}$ acyloxy groups such as acetoxy and propionyloxy; $C_{2-5}$ alkoxycarbonyloxy groups such as methoxycarbonyloxy and ethoxycarbonyloxy; $C_{1-4}$ alkylthio groups such as methylthio, ethylthio, i-butylthio, and t-butylthio; $C_{1-4}$ alkylsulfinyl groups such as methylsulfinyl, ethylsulfinyl, n-propylsulfinyl, and i-butylsulfinyl; $C_{1-4}$ alkylsulfonyl groups such as methylsulfonyl, ethylsulfonyl, i-butylsulfonyl, and n-butylsulfonyl; and $C_{7-12}$ aralkylthio groups such as benzylthio and naphthylmethylthio.

Preferred examples of A in the foregoing formulae are phenylene groups such as o-phenylene, and $C_{2-4}$ alkylene groups such as 1,2-ethylene and 1,3-propylene.

In the foregoing formula, $Y^1$ and $Y^2$ are the same or different and each represent independently oxygen or sulfur atom, with oxygen being preferred.

Examples of the electron withdrawing group as X in the foregoing formulae include cyano, nitro, alkoxycarbonyl (e.g. $C_{1-4}$ alkoxycarbonyl such as methoxycarbonyl and ethoxycarbonyl), hydroxycarbonyl, $C_{6-10}$ aryloxycarbonyl (e.g. phenoxycarbonyl), heterocycloxycarbonyl (as the heterocyclic group there may be used any of those exemplified above; e.g. pyridyloxycarbonyl, thienyloxycarbonyl), $C_{1-4}$ alkylsulfonyl (e.g. methylsulfonyl, trifluoromethylsulfonyl, ethylsulfonyl) which may be substituted with halogen (e.g. Cl, Br) for example, sulfamoyl, di-$C_{1-4}$ alkoxyphosphoryl (e.g. diethoxyphosphoryl), $C_{1-4}$ acyl (e.g. acetyl, trichloroacetyl, trifluoroacetyl) which may be substituted with halogen (e.g. Cl, Br) for example, carbamoyl, and $C_{1-4}$ alkylsulfonylthiocarbamoyl (e.g. methylsulfonylthiocarbamoyl). Nitro is one of preferred electron withdrawing groups.

$Z^1$ and $Z^2$ in the foregoing formulae are the same or different and represent each a halogen atom such as fluorine, chlorine, or bromine atom, or taken together represent an oxygen atom. Halogens, e.g. chlorine atom, are preferred examples of $Z^1$ and $Z^2$.

In the foregoing formulae, regarding the substituted or unsubstituted hydrocarbon radical in the definitions of $R^1$, $R^2$, $R^3$, $R^{1a}$ and $R^{3a}$, as examples of the hydrocarbon radical there are mentioned those referred to above in connection with the substituent R (particularly $C_{1-10}$ alkyl, $C_{2-10}$ alkenyl and $C_{2-10}$ alkynyl, which may be straight-chain, branched, or cyclic). As examples of the substituent group in the said "substituted or unsubstituted hydrocarbon residue" there are mentioned those exemplified above in connection with the substituent R. In the case where $R^1$ and $R^2$ taken together with the vicinal nitrogen represent a cyclic amino group, there are mentioned aziridino, azetidino, pyrrolidino, morpholino, and thiomorpholino, as examples of such cyclic amino group. As examples of the acyl group in the definitions of $R^{1a}$ and $R^3$ there are mentioned those exemplified above in connection with the substituent R.

As preferred examples of $R^1R^2N$ or $R^{1a}R^2N$ comprising $R^1$, $R^2$ and the vicinal nitrogen or $R^{1a}$, $R^2$ and the vicinal nitrogen there are mentioned unsubstituted amino groups, mono-$C_{1-4}$ alkyl amino groups such as methylamino, ethylamino and propylamino, and di-$C_{1-4}$ alkylamino groups such as dimethylamino and ethylmethylamino. In the case of $R^{1a}R^2N$, also preferred are acylamino groups such as formylamino and acetylamino, and N-$C_{1-2}$ acyl-N-$C_{1-4}$ alkylamino groups such as N-formyl-N-methylamino and N-acetyl-N-methylamino. Preferred examples of $R^3$ and $R^{3a}$ are hydrogen and $C_{1-4}$ alkyl groups such as methyl, ethyl and propyl. Formyl and acetyl groups are also preferred examples of $R^{3a}$.

In the foregoing formula, B represents a substituted or unsubstituted homocyclic or heterocyclic group. The homocyclic or heterocyclic group of B is a cyclic group containing only the same atoms, or a cyclic group containing two or more different kinds of atoms, and means a cyclic hydrocarbon radical or a heterocyclic group. Examples of the cyclic hydrocarbon group of B include $C_{3-8}$ cycloalkyl groups such as cyclopropyl, cyclobutyl, cyclopentyl, and cyclohexyl; $C_{3-8}$ cycloalkenyl groups such as cyclopropenyl, 1-cyclopentenyl, 1-cyclohexenyl, 2-cyclohexenyl, and 1,3-cyclohexadienyl; and $C_{6-14}$ aryl groups such as phenyl, 1- or 2-naphthyl, 1-, 2- or 9-anthryl, 1-, 2-, 3-, 4- or 9-phenanthryl, and 1-, 2-, 4-, 5- or 6-azulenyl. Preferred cyclic hydrocarbon radicals are aromatic, examples of which include $C_{6-14}$ aryl groups such as phenyl.

As the heterocyclic group of B there is used a five- to eight-membered ring group containing 1 to 5 hetero atoms such as oxygen, sulfur and nitrogen atoms, or a fused ring group thereof. Examples are 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, triazolyl, 1H- or 2H-tetrazolyl, N-oxide-2-, 3- or 4-pyridyl, 2-, 4- or 5-pyrimidinyl, N-oxide-2-, 4- or 5-pyrimidinyl, 3- or 4-pyridazinyl, pyrazinyl, N-oxide-2- or 3-pyrazinyl, N-oxide-3- or 4-pyridazinyl, benzofuryl, benzothienyl, benzothiazolyl, benzoxazolyl, triazinyl, oxo-triazinyl, tetrazolo [1,5-b]pyridazinyl, triazolo[4,5-b]pyridazinyl, oxo-imidazolyl, dioxo-triazinyl, pyrrolidinyl, piperidyl, pyranyl, thiopyranyl, 1,4-oxazinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, and phenoxazinyl. Five- or six-membered, nitrogen-containing heterocyclic groups such as 2-, 3- or 4-pyridyl and 2-, 4- or 5-thiazolyl are preferred. These homocyclic or heterocyclic groups may have to 5 (preferably 1) substituent groups which are the same or different. Examples of such substituent groups are those referred to above in connection with the substituent R.

Preferred examples of B are five- or six-membered, nitrogen-containing heterocyclic groups such as pyridyl and thiazolyl which may be substituted with one or two halogens.

The starting compound [II] used in the present invention can be prepared easily, for example by the process described in "Journal of American Chemical Society," Vol. 76, p. 1877, (1954), or a process similar thereto.

The reaction for deriving the compound [I] of the present invention from the compound [II] can be attained by the reaction of the compounds [II] and [III]. This reaction can be carried out using a suitable solvent. The solvent is not specially limited if only it does not afford a by-product through the reaction thereof with reaction substrate, reagent and product. But it is desirable to use a solvent which dissolves both reaction substrate and reagent. Examples of such solvent are aromatic hydrocarbons such as benzene, toluene and xylene; esters such as methyl acetate, ethyl acetate, ethyl formate, and ethyl propionate; ketones such as acetone and methyl ethyl ketone; ethers such as diethyl ether, dipropyl ether, dibutyl ether, tetrahydrofuran, and dioxane; nitriles such as acetonitrile and propionitrile; acid amides such as dimethyl formamide and dimethyl acetamide; sulfoxides such as dimethyl sulfoxide; sulfones such as sulforan; phosphoric acid amides such as hexamethyl phosphoramide; halogenated hydrocarbons such as dichloromethane, chloroform, 1,2-dichloroethane, and carbon tetrachloride; aromatic amines such as pyridine, picoline, lutidine, and quinoline; as well as mixtures thereof and mixtures thereof with water. Particularly preferred are pyridines such as pyridine, α-picoline, and 2,6-lutidine; nitriles such as acetonitrile; and halogenated hydrocarbons such as chloroform and dichloromethane.

For the purpose of accelerating the reaction or reducing the formation of by-product, the reaction may be performed in the presence of a base, or a base may be allowed to act before or after the reaction. As examples of the base, mention may be made of sodium hydride, sodium, alkali metal alcoholates such as sodium ethylate, sodium methylate, and potassium tert-butoxide, organic bases such as triethylamine, diisopropylethylamine, pyridine, and N,N-dimethylaniline, and inorganic bases such as potassium carbonate, sodium carbonate, sodium hydroxide, potassium hydroxide, sodium hydrogencarbonate, and potassium hydrogencarbonate. The amount of the base used is not specially limited if only it does not exert a bad influence on the reaction. For example, in the case of pyridine, it can be used in a large excess amount for serving as both base and solvent.

The amount of the compound [III] used as a reagent is in the range of 1 moles, preferably 1 to 2.5 moles, per mole of the compound [II].

The reaction temperature is usually in the range of −50° to 200° C., preferably −30° to 50° C. The reaction time is usually in the range of 0.1 to 24 hours, preferably 0.1 to 10 hours. The compound [I] obtained may be used as a starting material in the next reaction after isolation and purification by means known per se such as, for example, concentration vacuum concentration, redistribution, change of basicity, extraction with solvent, distillation, crystallization, recrystallization, or chromatography, or directly as the reaction mixture.

The di(thio)carboxylic acid derivative [III] used in the above process is in many cases a known compound. But, if necessary, it can be prepared by any of the methods described in "The chemistry of acid derivatives, part 1," JOHN WILEY & SONS (1979), Chapter 7; "The chemistry of acid derivatives, part 2," JOHN WILEY & SONS (1979), Chapter 11; and "The chemistry of acyl halides," JOHN WILEY & SONS (1972), Chapter 2, or a method similar thereto.

The reactions [I]→[V] and [I]→[VII] can be attained by reacting the compound [I] with an amine [IV] or a salt thereof or a cyclic amino compound [VI] or a salt thereof. These reactions can be carried out using a suitable solvent. The solvent is not specially limited if only it does not afford a by-product through the reaction thereof with reaction substrate, reagent and product. It is desirable to use a solvent which dissolves both reaction substrate and reagent. Examples of such solvent include aliphatic hydrocarbons such as pentane, hexane, heptane, petroleum ether; aromatic hydrocarbons such as benzene, toluene, and xylene; esters such as methyl acetate, ethyl acetate, ethyl formate, and ethyl propionate; ketones such as acetone and methyl ethyl ketone; ethers such as diethyl ether, dipropyl ether, dibutyl ether, tetrahydrofuran, and dioxane; alcohols such as methanol, ethanol, propanol, and butanol; nitriles such as acetonitrile and propionitrile; acid amides such as dimethylformamide and dimethylacetamide; sulfoxides such as dimethyl sulfoxide; sulfones such as sulforane; phosphoric acid amides such as hexamethylphosphoramide; halogenated hydrocarbons such as dichloromethane, chloroform, 1,2-dichloroethane, and carbon tetrachloride; aromatic amines such as pyridine, picoline, lutidine, and quinoline; as well as mixtures thereof and mixtures thereof with water.

The compound [IV] or a salt thereof or the compound [VI] or a salt thereof, as a reagent, can be used in an amount of 1 to 2 moles per mole of the compound [I]. But if the compound [IV] or a salt thereof is used in an excess amount, a bisamino derivative may be by-produced, so it is desirable to use it in an amount of 1 to 1.3 moles per mole of the compound [I]. The reaction temperature is usually in the range of −50° to 100° C., preferably −30° to 50° C., and the reaction time is usually in the range of 0.1 to 24 hours, preferably 0.1 to 10 hours. The resulting compound [V] or salt thereof or compound [VII] or salt thereof may be used as a starting material in the next reaction after isolation and purification by means known per se, e.g. concentration, vacuum concentration, redistribution, change of basicity, extraction with solvent, distillation, crystallization, recrystallization, or chromatography, or directly as the reaction mixture.

The amine [IV] or a salt thereof used in the above process can be prepared, for example by the method described in "Survey of Organic Synthesis," Wiley-Interscience (1970), Chapter 8, or a method similar thereto. And the cyclic amino compound [VI] or a salt thereof can be prepared, for example by the method described in "Organic Functional Group Preparations," Academic Press, Vol. 1, Chapter 13 (1968), and Vol.3, Chapter 10(1972), or by the method described in Japanese Patent Laid Open No. 171/1990, or a method similar thereto.

The reactions [V]→[VIII] and [VII]→[IX] can be attained by reacting the compound [V] or [VIII with [IV] or [VI] after acylation if necessary when $R^1$ and $R^3$ in the compound [V] or [VII] each represent a hydrogen atom. As a reagent in such acylation reaction there is used a known formylating agent such as, for example, formic acid, acetic formic anhydride, or formylimidazole, a known acetylating agent such as, for example, acetyl chloride or acetic anhydride, or other acylating agents.

The reactions in question can be conducted using a suitable solvent. The solvent is not specially limited if only it does not afford a by-product through the reaction thereof with reaction substrate, reagent and product. But a solvent which dissolves both reaction substrate and reagent is preferred. Examples of such solvent include aromatic hydrocarbons such as benzene, toluene, and xylene; esters such as methyl acetate, ethyl acetate, ethyl formate, and ethyl propionate; ketones such as acetone and methyl ethyl ketone; ethers such as diethyl ether, dipropyl ether, dibutyl ether, tetrahydrofuran, and dioxane; nitriles such as acetonitrile and propionitrile; acid amides such as dimethylformamide and dimethylacetamide; sulfoxides such as dimethyl sulfoxide; sulfones such as sulforane; phosphoric acid amides such as hexamethylphosphoramide; halogenated hydrocarbons such as dichloromethane, chloroform, 1,2-dichloroethane, and carbon tetrachloride; aromatic amines such as pyridine, picoline, lutidine, and quinoline; as well as mixtures thereof and mixtures thereof with water. Particularly preferred are pyridines such as pyridine, α-picoline, and 2,6-lutidine; nitriles such as acetonitrile; and halogenated hydrocarbons such as chloroform and dichloromethane.

With a view to accelerating the reaction or reducing the formation of by-product, the reaction may be performed in the presence of a base, or a base may be allowed to act before or after the reaction. As examples of the base there are mentioned alkali metal alcoholates such as sodium ethylate, sodium methylate, and potassium tert-butoxide; organic bases such as triethylamine, diisopropylethylamine, pyridine, and N,N-dimethylaniline; and inorganic bases such as potassium carbonate, sodium carbonate, sodium hydroxide, potassium hydroxide, sodium hydrogencarbonate, and potassium hydrogen-carbonate. The amount of the base used is not specially limited if only it does not badly influence the reaction. For example, in the case of pyridine, it can be used in a large excess amount for serving as both base and solvent. The amount of the acylating agent used in the reaction is in the range of 1 to 5 moles, preferably 1 to 2.5 moles, per mole of the compound [V] or [VII].

The reaction temperature is usually in the range of −50° to 200° C., preferably −30° to 50° C., and the reaction time is usually in the range of 0.1 to 24 hours, preferably 0.1 to 10 hours. The resulting compound may be used as a starting material in the next reaction after isolation and purification by means known per se, e.g. concentration, vacuum concentration, redistribution, change of basicity, extraction with solvent, distillation, crystallization, recrystallization, or chromatography, or directly as the reaction mixture.

In the reaction [V]→[VIII], as examples of RS in the compound [V] or a salt thereof, $C_{1-4}$ alkylthio groups such as methylthio, and $C_{7-10}$ aralkylthio groups such as benzylthio, are particularly preferred. It is preferable that the compound [VI] or a salt thereof be used in an amount of about 0.8 to 2.0 equivalents based on the amount of the compound [V] or a salt thereof. But the compound [VI] or a salt thereof may be used in an amount of about 2.0 to 20 equivalents if this amount does not impede the reaction.

The reaction may be performed in the absence of solvent, but usually the reaction is carried out in a suitable solvent. Examples of such solvent include water, alcohols such as methanol, ethanol, n-propanol, and isopropanol; aromatic hydrocarbons such as benzene, toluene, and xylene; halogenated hydrocarbons such as dichloromethane and chloroform; saturated hydrocarbons such as hexane, heptane, and cyclohexane; ethers such as diethyl ether, tetrahydrofuran, and dioxane; ketones such as acetone; nitriles such as acetonitrile; sulfoxides such as diemthyl sulfoxide; acid amides such as N,N-dimethylformamide; esters such as ethyl acetate; and carboxylic acids such as acetic acid and propionic acid. These solvents may be used each alone or, if necessary, may be used as a mixture of two or more kinds in a suitable ratio, for example in the range of 1:1 to 1:10. In the case where the reaction mixture is not a homogeneous phase mixture, the reaction may be carried out in the presence of an inter-phase transfer catalyst such as a quaternary ammonium salt, e.g. triethylbenzylammonium chloride, tri-n-octylmethylammonium chloride, trimethyldecylammonium chloride, or tetramethylammonium bromide, or a crown ether.

This reaction may be accelerated by the addition of a base or a metallic salt in an amount of 0.01 to 10 equivalents, preferably 0.1 to 3 equivalents. As examples of such base there are mentioned inorganic bases such as sodium hydrogen-carbonate, potassium hydrogencarbonate, sodium carbonate, potassium carbonate, sodium hydroxide, potassium hydroxide, calcium hydroxide, phenyllithium, butyllithium, sodium hydride, potassium hydride, sodium methoxide, sodium ethoxide, metal sodium, and metal potassium, as well as organic bases such as triethylamine, tributylamine, N,N-dimethylaniline, pyridine, lutidine, collidine, 4-(dimethylamino)pyridine, and DBU(1,8-diazabicyclo[5,4,0]undecene-7). These organic bases per se can also be used as solvents. Examples of employable metallic salts include copper salts such as copper chloride, copper bromide, copper acetate, and copper sulfate, as well as mercury salts such as mercury chloride, mercury nitrate, and mercury acetate.

In this reaction, the reaction temperature is usually in the range of −20° to 150° C. and the reaction time is usually in the range of 10 minutes to 50 hours, but preferably 0° to 100° C. and 1 to 20 hours, respectively.

In the reaction [VII]→[IX], preferred examples of RS and reaction conditions are the same as those mentioned in connection with the reaction [V]→[VIII].

In each of the reactions [I]→[V] and [I]→[VII] there is by-produced an imide compound represented by the following formula:

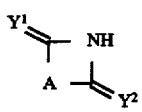

In many cases, the compound [V] or [VII] and the imide compound can be separated from each other by a known means, e.g. chromatography. But if the separation is difficult, it is possible to separate the two by using a method wherein the reaction mixture is dissolved in a basic aqueous solution and the compound [V] or [VII] and the imide compound are subjected to fractional precipitation while neutralization is allowed to proceed little by little by using an acid, or by adopting a method wherein the imide compound is decomposed into, for example, di(thio) carboxylic acid monoamide derivative by stirring in a basic aqueous solution, followed by neutralization with an acid to precipitate IV] or [VII]. As examples of bases employable in these separation methods there are mentioned inorganic bases such as sodium carbonate, potassium carbonate, sodium hydroxide, potassium hydroxide, and calcium hydroxide, as well as organic bases such as triethylamine, tributylamine, N,N-dimethylaniline, pyridine, lutidine, collidine, 4-(dimethylamino)pyridine, and DBU(1,8-diazabicyclo[5,4,0]undecene-7). Examples of the acid used for neutralization in the above methods include inorganic acids such as hydrochloric acid, hydrobromic acid, hydriodic acid, phosphoric acid, sulfuric acid, and perchloric acid, as well as organic acids such as formic acid, acetic acid, tartaric acid, malic acid, citric acid, oxalic acid, succinic acid, beznoic acid, picric acid, and p-toluenesulfonic acid.

The above separation methods may each be used as a separation method for the compound [VIII] or [IX] and the imide compound after completion of such two-step reaction as [I]→[V]→[VIII] or [I]→[VII]→[IX].

The resulting compound [VIII] or [IX] or a salt thereof can be isolated and or purified by means known per se, e.g. concentration, vacuum concentration, redistribution, change of basicity, extraction with solvent, crystallization, recrystallization, or chromatography.

As the case may be, the compounds [I] and/or [V] and/or [VI] and/or [VII] can be converted into the desired products [VIII] and/or [IX] after transient isolation, or in situ. The compounds [VIII] and/or [IX] may be prepared via the compound [I] from the starting compounds [II] and [III] without the purification and/or isolation of the intermediates.

In the case where the resulting guanidine derivative [VIII] or [IX] is obtained as a free compound, this compound can be converted by a conventional method into a salt thereof with an inorganic acid such as, for example, hydrochloric acid, hydrobromic acid, hydriodic acid, phosphoric acid, sulfuric acid, or perchloric acid, or an organic acid such as, for example, formic acid, acetic acid, tartaric acid, malic acid, citric acid, oxalic acid, succinic acid, benzoic acid, picric acid, or p-toluenesulfonic acid.

In the case where $R^3$ (or $R^{3a}$) is hydrogen and $R^1$ (or $R^{1a}$) or $R^2$ is hydrogen, the compound in question can be converted by a conventional method into a metallic salt thereof such as, for example, sodium salt, potassium salt, or lithium salt, or an organic base such as, for example, triethylammonium salt or tetrabutylammonium salt.

In the case where the guanidine derivative is obtained in the form of a salt, it can be converted into a free compound by a conventional method. As salts of the compounds [IV], [V], [VI] and [VII] there may be used such salts as mentioned above in connection with [VIII] or [IX].

In the guanidine derivative [VIII] or [IX] or a salt thereof, there are formed stereoisomers of cis and trans forms with respect to the position of the substituent X, while when $R^3$ (or $R^{3a}$) is hydrogen and when $R^1$ (or $R^{1a}$) or $R^2$ is hydrogen, there are formed tautomers theoretically. These isomers are all included in the compound [VIII] or [IX] or a salt thereof according to the present invention.

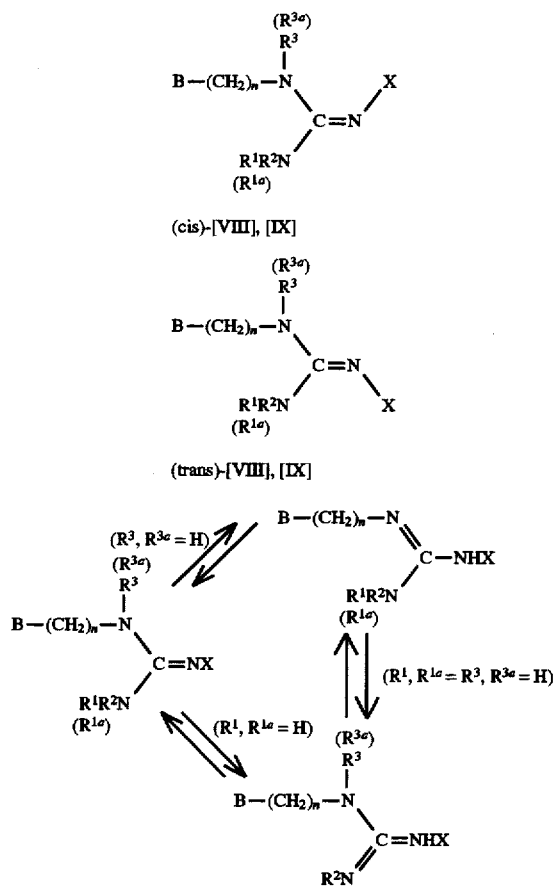

The guanidine derivative [VIII] or [IX] and salts thereof are effective in the control of sanitary insect pests and animal/plant parasitic insects, and exhibit a strong insecticidal action when contacted directly with insects, for example by being sprinkled directly over animals and plants with insect pests parasitic thereon. But a more characteristic point resides in that they exhibit a strong insecticidal action also when they are once absorbed into a plant through the root, leaves, or stalk of the plant and thereafter an insect pest sucks or chews the plant or comes into contact with the plant. This property is advantageous in exterminating sucking or chewing insect pests. Besides, the compounds [VIII], [IX] and salts thereof are low in chemical injury against plants and also low in toxicity against fish. Thus, they possess safe and advantageous properties as insect pest control agents for sanitation, horticulture, particularly for agriculture.

In using the guanidine derivative [VIII] or [IX] or a salt thereof as an insecticide, it is used in any of the forms which conventional agricultural chemicals can take. More specifically, one or more of these compounds and salts thereof are dissolved or dispersed in a suitable liquid, or mixed with or adsorbed on a suitable solid carrier, according to purposes of use, and are used in a suitable formulation such as, for example, emulsion, oil, hydrate, powder, granules, tablets, aerosol, or ointment. These formulations can be prepared by a method known per se. If necessary, emulsifier, suspending agent, spreader, penetrant, wetting agent, mucilage, and stabilizer, may be incorporated therein.

The contents of active constituents in the insecticide differ according to purposes of use, but in the case of emulsion and hydrate, a suitable content of active constituents is in the range of 10 to 90 wt %; in the case of oil and powder, a suitable content thereof is 0.1 to 10 wt %; further, in the case of granules, 1 to 20 wt % is suitable. The concentration of active constituents may be changed according to purposes of use. Emulsion and hydrate are sprinkled after diluted for extension (e.g. 100 to 100,000X) using water for example.

Suitable examples of the liquid carrier (solvent) used are water, alcohols (e.g. methyl alcohol, ethyl alcohol, n-propyl alcohol, isopropyl alcohol, ethylene glycol), ketones (e.g. acetone, methyl ethyl ketone), ethers (e.g. dioxane, tetrahydrofuran, ethylene glycol monomethyl ether, diethylene glycol monomethyl ether, propylene glycol monomethyl ether), aliphatic hydrocarbons (e.g. kerosene, fuel oil, machine oil), aromatic hydrocarbons (e.g. benzene, toluene, xylene, solvent naphtha, methylnaphthalene), halogenated hydrocarbons (e.g. dicholoromethane, chloroform, carbon tetrachloride), acid amides (e.g. dimethylformamide, dimethylacetamide), esters (e.g. ethyl acetate, butyl acetate, fatty acid glycerin ester), and nitriles (e.g. acetonitrile, propionitrile). One or more of these solvents may be mixed in a suitable ratio.

Examples of the solid carrier (diluent/extender) include vegetable powders (e.g. soybean meal, tobacco power, wheat flour, wooden powder), mineral powders (e.g. clays such as kaolin, bentonite, terra alba, talcs such as talcum powder and agalmatolite powder, and silicas such as diatomaceous earth and mica powder), alumina, sulfur powder, and active carbon. One or more of these solid carriers may be mixed in a suitable ratio.

Examples of ointment bases are polyethylene glycol, pectin, polyhydric alcohol esters of higher fatty acids such as monostearic acid glycerin ester, cellulose derivatives such as methyl cellulose, sodium alginate, bentonite, higher alcohols, polyhydric alcohols such as glycerin, vaseline, white petrolatum, liquid paraffin, lard, various vegetable oils, hydrous lanolin, anhydrous lanolin, hardened oil, and resins. One or more of these ointment bases are employable. Various surfactants such as those exemplified below may be incorporated therein.

As examples of surfactants used as emulsifiers, spreaders, penetrants, or dispersants, there are mentioned nonionic and anionic surfactants such as soaps, polyoxyethylene alkylaryl ethers (e.g. Noigen®, E.A 142®, products of Dai-ichi Kogyo Seiyaku K.K.; Nonal®, a product of Toho Kagaku K.K.), alkylsulfates (e.g. Emal 10® and Emal 40®, products of Kao K.K.), alkylsulfonates (e.g. Neogen® and Neogen T®, products of Dai-ichi Kogyo Seiyaku K.K.; Neopellex, a product of Kao K.K.), polyethylene glycol ethers (e.g. Nonipol 85®, Nonipol 100® and Nonipol 160®, products of Sanyo Kasei K.K.), and polyhydric alcohol esters (e.g. Tween 20® and Tween 80®, products of Kao K.K.).

The guanidine derivative [VIII] or [IX] or a salt thereof may be mixed with other kinds of insecticides pyrethroid-based insecticides, organophosphorus-based insecticides, carbamate-based insecticides, natural insecticides), miticide, nematicide, herbicide, plant hormone, plant growth regulator, fungicide (e.g. copper-based fungicide, organochlorine-based fungicide, organosulfur-based fungicide, phenolic fungicide), synergist, attractant, repellent, pigment, fertilizer and manure.

Insecticides containing the guanidine derivatives [VIII], [IX], and/or salts thereof are effective particularly in the control of Hemiptera pests such as, for example, *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae,* and *Aphis gossypii*; Lepidoptera pests such as, for example, *Spodoptera litura, Plutella xylostella, Pieris rapae crucivora, Chilo suppressalis, Autographa nigrisigna, Helicoverpa assulta, Pseudaletia Separata, Mamestra brassicae, Adoxophyes orana fasciata, Notarcha derogata, Cnaphalocrocis medinalis,* and *Phthorimaea operculella*; Coleoptera pests such as, for example, *Epilachna vigintioctopunctata, Aulacophora femoralis, Phyllotreta striolata, Oulema oryzae,* and *Echinocnemus squameus*; Diptera pests such as, for example, *Musca domestica, Culex pipiens pallens, Tabanus trigonus, Delia antiqua,* and *Delia platura*; Orthoptera pests such as, for example, *Locusta migratoria* and *Gryllotalpa africana*; Blattidae pests such as, for example, *Blattella germanica* and *Periplaneta fuliginosa*; acaridan pests such as, for example, *Tetranychus urticae, Panonychus citri, Tetranychus kanzawai, Tetranychus cinnabarinus, Panonychus ulmi,* and *Aculops pelekassi*; and Nematoda such as, for example, *Aphelenchoides besseyi*.

The insecticide thus obtained is extremely low in toxicity and is a safe and excellent agricultural chemical. It can be used in the same manner as in conventional insecticides and so can exhibit superior effects in comparison with conventional products. For example, the insecticide of the present invention can be used in the mode of raising seedling box treatment, sprinkling over stalks and leaves of crop, sprinking to insects, underwater application in paddy field, or soil treatment. Its amount to be used can be changed over a wide range, depending on when, where and how it is to be used. Preferably, the insecticide of the invention is used in such a manner that the proportion of active constituent (guanidine derivative [VIII] and/or a salt thereof) is in the range of 0.3 to 3,000 g, more preferably 50 to 1,000 g, per hectare. In the case where the insecticide of the present invention is in the form of a hydrate, it may be diluted before use so that the final concentration of active constituent is in the range of 0.1 to 1,000 ppm, preferably 10 to 500 ppm.

EXAMPLES

Working examples of the present invention will be given below to illustrate the invention in more detail, but it is to be understood that the invention is not limited thereto.

In the Working Examples and Reference Example, the elution in column chromatography was performed under observation using TLC (Thin Layer Chromatography). In the TLC observation, Kiesel gel 60F$_{254}$ (70–230 mesh, a product of Merck Co.) was used as a TLC plate; the solvent used as an eluant in column chromatography was used as a developing solvent; and a UV detector was used for detection. Further, as a silica gel for column chromatography there was used Kieselgel 60 (70–230 mesh, a product of Merck Co.). NMR spectrum represents proton NMR, there was used tetramethylsilane as an internal reference standard, measurement was made using a VARIAN EM390 (90 MHz) type or Hitachi R-600 (60 MHz) type spectrometer, and all δ values were shown in terms of parts per million (ppm). Each parenthesized value in the case of using a mixed solvent as a developing solvent represents a volume ratio of the ingredients thereof.

The abbreviations used in the following Examples and Table-1 have the following meanings.

Me: methyl, Et: ethyl, Ph: phenyl, s: singlet, br: broad, d: doublet, t: triplet, q: quartet, m: multiplet, dd: doublet of doublets, J: coupling constant, Hz: hertz, CDCl$_3$:deuteriochlorofrom, DMSO-d$_6$: deuteriodimethylsulfoxide, %: wt %, mp: melting point. "Room temperature" indicates about 15°–25° C.

Example 1

A mixture consisting of 5 g S-methyl-N-nitroisothiourea and 70 ml pyridine was ice-cooled, into which was then added 14.5 g of phthaloyl chloride dropwise over a period of 30 minutes. After stirring for 10 minutes under ice-cooling, the reaction mixture was poured into an ice-cooled, diluted hydrochloric acid (concentrated hydrochloric acid 100 ml, water 500 ml) and the resulting crystals were collected by filtration. Then, 50 ml of EtOH was added for recrystallization to afford 8.0 g of S-methyl-N-nitro-N'-Phthaloylisothiourea as white needle-like crystals, mp 138°–140° C.

$^1$H-NMR(CDCl$_3$): 8.10–7.80 (4H, m), 2.64 (3H, s)

Example 2

A mixture consisting of 2 g S-methyl-N-nitro-N'-phthaloylisothiourea and 20 ml acetonitrile was ice-cooled, into which was then added 1.1 g of 2-chloro-5-(aminomethyl)thiazole dropwise over a 10 minute period. After stirring for 30 minutes under ice-cooling, the reaction mixture was concentrated and the residue was purified by column chromatography [eluent: chloroform-ethanol (20:1)] to afford 1.93 g of N-(2-chloro-5-thiazolylmethyl)-S-methyl-N'-nitroisothiourea as a light yellow powder, mp 162.5°–165° C.

$^1$H-NMR(DMSO-d$_6$): 9.20–8.60 (1H, br), 7.53 (1H, s), 4.72 (2H, d, J=5.0 Hz), 2.44 (3H, s)

Example 3

A mixture consisting of 300 mg S-methyl-N-nitro-N'-phthaloylisothiourea and 10 ml acetonitrile was ice-cooled, into which was then added 150 mg of benzylamine dropwise over a 10 minute period. After stirring for 15 minutes under ice-cooling, the reaction mixture was concentrated and the residue was purified by column chromatography [eluent: n-hexane-ethyl acetate (1:1)] to afford 248 mg of N-benzyl-S-methyl-N'-nitroisothiourea as a white powder, mp 77°–80° C.

$^1$H-NMR(DMSO-d$_6$): 10.20–8.20 (1H, br), 7.32 (4H, s), 4.64 (2H, S), 2.46 (3H, s)

Example 4

349 mg of a 40% methylamine methanol solution was dropwise added to a mixture consisting of ] g N-(2-chloro-5-thiazolylmethyl)-S-methyl-N'-nitroisothiourea and 30 ml acetonitrile, at room temperature, over 5 minutes. After stirring for 1.5 hours, the resultant white precipitate was collected by filtration and then dried to afford 410 mg of N-(2-chloro-5-thiazolylmethyl)-N'-methyl-N"-nitroguanidine (compound No. 14) as a white powder. The mother liquor after the filtration was concentrated, then 20 ml of ethanol was added, followed by stirring thoroughly, and the crystals formed were collected by filtration to obtain additional 330 mg of compound No.14 (mp 172°–173° C). Upon recrystallization from acetonitrile, this product exhibited mp 173°–174° C.

$^1$H-NMR(DMSO-d$_6$): 9.15–8.75 (1H, br), 7.58 (1H, s), 8.25–7.90 (1H, br), 4.51 (2H, d, J=5.0Hz), 2.84 (3H, d, J=5.0Hz)

Example 5

A mixture consisting of 10 g S-methyl-N-nitro-N'-phthaloylisothiourea and 100 ml acetonitrile was ice-cooled, into which was then added 5.6 g of 2-chloro-5-(aminomethyl) thiazole dropwise over a 10 minute period. After stirring for 30 minutes under ice-cooling, the temperature was raised to room temperature, and 3.5 g of a 40% methylamine methanol solution was dropwise added over 5 minutes. After stirring for 1.5 hours, the reaction mixture was concentrated to afford 14.9 g of a mixture consisting of N-(2-chloro-5-thiazolylmethyl)-N'-methyl-N"-nitroguanidine (compound No.14) and phthalimide, as a white powder. This white powder was dissolved in an aqueous potassium hydroxide solution (potassium hydroxide 8.5 g, water 80 ml). Subsequent 1 hour stirring at room temperature was followed by ice-cooling, and then 8 ml of concentrated hydrochloric acid was added little by little. After stirring for another 30 minutes under ice-cooling, the resultant crystals were collected by filtration and dried to give 8.8 g of compound as a light yellow powder. This product was the same in melting point, NMR, IR and TLC Rf values as the compound obtained in Example 4.

Example 6

252 mg of a 50% aqueous dimethylamine solution was dropwise added to a mixture consisting of 600 mg N-(2-chloro-5-thiazolylmethyl)-g-methyl-N'-nitroisothiourea and 20 ml acetonitrile at room temperature. After stirring at room temperature for 2 hours, the reaction mixture was concentrated and 20 ml of ethanol was added to the residue, followed by stirring thoroughly. The resultant crystals were collected by filtration and dried to afford 350 mg of N-(2-chloro-5-thiazolylmethyl)-N',N'-dimethyl-N"-nitroguanidine (compound No. 17) as a white powder. The mother liquor after the filtration was concentrated and 5 ml of ethanol was added, followed by stirring thoroughly, then the resultant crystals were collected by filtration and dried to give additional 120 mg of compound No. 17 (mp 154°–159° C.). Recrystallization of this product from acetonitrile afforded a product having a melting point of 164°–166° C.

$^1$H-NMR(DMSO-d$_6$): 8.70–8.35 (1H, br), 7.51 (1H, s), 4.53 (2H, br), 3.00 (6H, s)

Example 7

A mixture consisting of 0.5 g S-methyl-N-nitroisothiourea, 1.5 g potassium carbonate and 30 ml acetonitrile was ice-cooled and 1.5 g of succinic acid chloride was added to the ice-cooled mixture dropwise over 2 minutes. After stirring for 1 hour under ice-cooling, there was made stirring for additional 30 minutes at room temperature. Insolubles were filtered off and thereafter the solvent was distilled off, while the residue was dissolved in chloroform, washed with aqueous sodium bicarbonate, then dried over anhydrous magnesium sulfate and concentrated. The residue was purified by column chromatography [eluent: chloroform-ethanol (10:1)] to give 0.28 g of S-methyl-N-nitro-N'-succinylisothiourea as a white powder, mp 114°–115° C.

$^1$H-NMR(CDCl$_3$): 2.90 (4H, s), 2.60 (3H, s)

Example 8

A mixture consisting of 210 mg S-methyl-N-nitro-N'-succinylisothiourea and 10 ml acetonitrile was ice-cooled and 160 mg of 2-chloro-5-(aminomethyl)thiazole was added to the ice-cooled mixture over 30 seconds. After stirring for 10 minutes under ice-cooling, the solvent was distilled off and the residue was washed with 12 ml of water, then the resultant crystals were collected by filtration and air-dried to give 220 mg of N-(2-chloro-5-thiazolylmethyl)-S-methyl-N'-nitroisothiourea as a yellow powder. This product was the same in melting point, NMR, IR and TLC Rf values as the compound obtained in Example 2.

Example 9

A mixture consisting of 0.5 g S-methyl-N-nitroisothiourea, 1.03 g potassium carbonate and 10 ml acetonitrile was ice-cooled and 1.65 g of glutaric acid chloride was added to the ice-cooled mixture dropwise over 2 minutes. After stirring for 1 hour under ice-cooling, there was made stirring for another 1 hour at room temperature. Insolubles were filtered off and the solvent was distilled off, then the residue was purified by column chromatography [eluent: chloroform-ethanol (10:1)] to give 0.22 g of N-glutaryl-S-methyl-N'-nitroisothiourea as a white powder, mp 147°–149° C.

$^1$H-NMR(CDCl$_3$): 2.70 (t, 4H), 2.60 (s, 3H), 1.70–2.30 (m, 2H)

Example 10

A mixture consisting of 0.18 g N-glutaryl-S-methyl-N'-nitroisothiourea and 10 ml acetonitrile was ice-cooled and 0.1 g of 2-chloro-5-(aminomethyl)thiazole was dropwise added to the ice-cooled mixture. After stirring for 30 minutes under ice-cooling, there was made stirring for additional 1 hour at room temperature. The solvent was distilled off and then the residue was purified by column chromatography [eluent: chloroform-ethanol (10:1)] to yield 170 mg of N-(2-chloro-5-thiazolylmethyl)-S-methyl-N'-nitroisothiourea as a white powder. This product was the same in melting point, NMR, IR and TLC Rf values as the compound obtained in Example 2.

Example 11

A mixture consisting of 0.5 g S-methyl-N-nitroisothiourea, 2.06 g potassium carbonate, 30 ml acetonitrile and 1 ml water was ice-cooled and 1.55 g of cis-1,2-cyclohexanedicarboxylic acid chloride was dropwise added to the ice-cooled mixture over 1 minute. After stirring for 20 minutes under ice-cooling, there was made stirring for additional 1 hour at room temperature. Then, 30 ml of water and 30 ml of chloroform were added to the reaction mixture for separation into layers. The resultant aqueous layer was extracted using 100 ml of chloroform, while organic layers were combined together, dried and then concentrated. The residue was purified by column chromatography [eluent: chloroform-ethanol (10:1)] to yield 270 mg of N-(cyclohexane-cis-1,2-dicarbonyl)-S-methyl-N'-nitroisothiourea as a white powder, mp 112°–113° C.

$^1$H-NMR(CDCl$_3$): 2.90–3.20 (m, 2H), 2.60 (s, 3H), 1.30–2.10 (m, 8H)

Example 12

A mixture consisting of 370 mg N-(cyclohexane-cis-1,2-dicarbonyl)-S-methyl-N'-nitroisothiourea and 10 ml acetonitrile was ice-cooled and 223 mg of 2-chloro-5-(aminomethyl)thiazole was dropwise added to the ice-cooled mixture. After stirring for 30 minutes under ice-cooling, there was made stirring for additional 1 hour at room temperature. The solvent was distilled off and the residue was purified by column chromatography [eluent: chloroform-ethanol (10:1)] to afford 170 mg of N-(2-chloro-5-thiazolylmethyl)-S-methyl-N'-nitroisothiourea as a white powder. This product was the same in melting point, NMR, IR and TLC Rf values as the compound obtained in Example 2.

Example 13

A mixture of 0.5 g S-methyl-N-nitroisothiourea and 20 ml pyridine was heated to 62° C. and a solution of 1.27 g diglycolic acid dichloride in 2 ml acetonitrile was added to the ice-cooled mixture dropwise over 1 minute. After heating and stirring for 80 minutes, the reaction mixture was added into dilute hydrochloric acid (concentrated hydrochloric acid 50 ml, water 50 ml, ice 20 g) and extracted using 90 ml of chloroform. The chloroform layer was washed with 30 ml of aqueous sodium bicarbonate, followed by drying over magnesium sulfate. Subsequent concentration afforded an oily product, to which was then added a small amount of ethyl acetate, followed by stirring. As a result, crystals were precipitated, which were then collected by filtration to yield 440 mg of S-methyl-N-nitro-N'-(2,2'-oxydiacetyl)-isothiourea as white crystals, mp 132°–134° C.

$^1$H-NMR(CDCl$_3$): 4.40 (s, 4H), 2.65 (s, 3H)

Example 14

A mixture consisting of 90 mg S-methyl-N-nitro-N'-(2,2'-oxydiacetyl)isothiourea and 9 ml chloroform was ice-cooled and a solution of 100 mg 2-chloro-5-(aminomethyl)thiazole in 0.5 ml chloroform was dropwise added to the ice-cooled mixture. After stirring for 20 minutes under ice-cooling and 50 minutes at room temperature, there were added 15 ml of water and 15 ml of chloroform for separation into layers. The resultant aqueous layer was extracted using 50 ml of chloroform, while the resultant organic layers were combined together, the solvent was distilled off and the residue was purified by column chromatography [eluent: chloroform-ethanol (10:1)] to afford 30 mg of N-(2-chloro-5-thiazolylmethyl)-S-methyl-N'-nitroisothiourea as a white powder. This product was the same in melting point, NMR, IR and TLC Rf values as the compound obtained in Example 2.

Example 15

Into a mixture of 1 g S-methyl-N-nitroisothiourea, 6.15 g potassium carbonate and 100 ml acetonitrile was added dropwise 2.7 g of adipic acid dichloride over 5 minutes while the mixture was stirred at room temperature. After stirring for 2 hours, the resultant crystals were recovered by filtration and washed with a small amount of acetonitrile to give 470 mg of N-adipoyl-S-methyl-N'-nitro-isothiourea as white crystals, mp 193°–194° C.

$^1$H-NMR(CDCl$_3$): 3.00–2.20 (m, 4H), 2.40 (s, 3H), 2.00–140 (m, 4H)

Example 16

Into a mixture of 300 mg S-methyl-N-nitro-N'-succinylisothiourea and 5 ml acetonitrile was added dropwise 236 mg of (6-chloro-3-pyridyl)methylethylamine under ice-cooling. After stirring at room temperature for 13 hours, the reaction mixture was concentrated and the residue was dissolved in 100 ml of ethyl acetate, followed by washing with two 50 ml portions of water. The resultant organic layers were concentrated to give 350 mg of N-(6-chloro-3-pyridylmethyl)-N-ethyl-S-methyl-N'-nitroisothiourea as a light brown oil.

$^1$H-NMR(CDCl$_3$): 8.33(1H,br), 7.73(]H,dd,J=9.0Hz,2.5 Hz), 7.36(]H,d,J=9.0Hz), 4.83(2H,s), 3.65(2H,q), 2.57(3H, s), 1.29(3H,t)

Example 17

(6-Chloro-3-pyridyl)methylamine (197 mg) was dropwise added under ice-cooling into a mixture consisting of 300 mg S-methyl-N-nitro-N'-succinylisothiourea and 5 ml acetonitrile. After stirring for 1 hour under ice-cooling, the reaction mixture was concentrated and 30 ml of water was added to the residue, followed by stirring thoroughly. The resultant crystals were collected by filtration and dried to yield 360 mg of N-(6-chloro-3-pyridylmethyl)-S-methyl-N'-nitroisothiourea, mp 140°–141.5° C.

$^1$H-NMR(CDCl$_3$+DMSO-d$_6$): 9.60–8.90 (1H,br), 8.40 (1H,br), 7.78 (1H,dd,J=9.0Hz, 2.5 Hz), 7.33(1H,d,J=9.0Hz), 4.63(2H,s), 2.48 (3H,s)

Example 18

To a mixture of 1 g N-(2-chloro-5-thiazolylmethyl)-S-methyl-N'-nitroisothiourea, 560 mg potassium carbonate, 400 mg cuprous chloride and 12 ml acetonitrile was added 610 mg of 2-chloro-5-(aminomethyl)thiazole and the mixture was stirred for 1 hour under reflux. Thereafter, the reaction mixture was concentrated, then water was added to the resultant solids, followed by stirring thoroughly. Thereafter, the solids were collected by filtration and purified by column chromatography [eluent: dichloromethane-methanol (10:1)] to afford 191 mg of N,N'-bis(2-chloro-5-thiazolylmethyl)-N''-nitroguanidine (compound No.39) as a white powder, mp 217°–218° C.

$^1$H-NMR(DMSO-d$_6$): 8.95 (2H,br), 7.59 (2H,s), 4.60(4H, br)

Example 19

A mixture consisting of 1 g N-(2-chloro-5-thiazolylmethyl)-S-methyl-N'-nitroisothiourea, 1.15 g acetic anhydride and 25 ml pyridine was stirred at room temperature for 3 hours. The reaction mixture was added into an aqueous hydrochloric acid solution (concentrated hydrochloric acid 20 ml, water 50 ml, ice 10 g) for separation into layers. The resultant aqueous layer was extracted with 120 ml of chloroform, while the resultant organic layers were combined together, dried over magnesium sulfate and concentrated to afford 1.15 g of N-acetyl-N-(2-chloro-5-thiazolylmethyl)-S-methyl-N'-nitroisothiourea as a brown crystal, mp 77°–78° C.

$^1$H-NMR(CDCl$_3$): 7.50 (1H, s), 4.80 (2H, s), 2.52 (3H, s), 2.26 (3H, s)

Then, a solution of 130 mg 40% methylamine methanol solution in 3 ml chloroform was dropwise added into a mixture of 0.5 g of the compound thus prepared and 7 ml of chloroform under stirring at −15° C. stirring was made for 2 hours while the temperature was raised gradually, then the reaction mixture was concentrated and purified by column chromatography [eluant: chloroform-ethanol(10:1)] to afford 180 mg of N-acetyl-N-(2-chloro-5-thiazolylmethyl)-N'-methyl-N''-nitroguanidine (compound No.38) as a white powder, mp 105°–106° C.

$^1$H-NMR(CDCl$_3$): 7.50 (1H, s), 4.90 (2H, s), 3.05 (3H, s), 2.25 (3H, s)

Example 20

To a mixture of S-methyl-N-nitro-N'-phthaloylisothiourea (20 g) and toluene (300 ml) was added dropwise 40% solution of methylamine in methanol at −7° C. over 30 minutes. The mixture was stirred at −7° C. over 30 minutes and the resulting crystals were separated by filtration and dried by air to yield 19.7 g of white crystals. The toluene filtrate was concentrated to give 2.7 g of yellow crystals. These crystals were combined and dissolved in an aqueous solution of potassium hydroxide (potassium hydroxide, 16.9 g and water, 160 ml). The solution was stirred at room temperature for 1 hour, and cooled with ice, into which was then added dropwise 16 ml of concentrated hydrochloric acid. The mixture was stirred for 10 minutes under ice-cooling and the resulting crystals were collected by filtration and dried to afford 9.8 g of N,S-dimethyl-N'-nitroisothiourea as a pale yellow powder, mp 150°–152° C.

$^1$H-NMR(DMSO-d$_6$): 8.30–8.95 (1H, br), 2.94 (3H, s, NMe), 2.44 (3H, s, SMe)

Example 21

To a mixture of N,S-dimethyl-N'-nitroisothiourea (500 mg), potassium carbonate (695 mg) and acetonitrile (10 ml) was added 376 mg of acetic anhydride at room temperature. After stirring at room temperature for 5 hours, 10 ml of 2N hydrochloric acid was added to the mixture which was then extracted with 40 ml of dichloromethane. The resultant organic layers were washed with aqueous saturated sodium bicarbonate, then dried over anhydrous magnesium sulfate and concentrated to afford 600 mg of N-acetyl-N,S-dimethyl-N'-nitroisothiourea as a white crystal, mp 40°–41° C.

$^1$H-NMR(CDCl$_3$): 2.23(3H, s), 2.52 (3H, s), 3.17 (3H, s)

To a mixture of the compound thus obtained (300 mg), and dichloromethane (5 ml) was added dropwise a solution of 5-(aminomethyl)-2-chlorothiazole (241 mg) in ] ml of diohloromethane at −10° C. After stirring at −10° C. for 2 hours, 10 ml of 2N hydrochloric acid was added to the mixture. The resultant organic layers were separated by partition, dried over anhydrous magnesium sulfate and concentrated to afford 430 mg of colorless oily products. The product was dissolved in 5 ml of toluene and 5 ml of n-hexane was added to the solution before vigorously stirring. White precipitates were formed by such treatments, collected by filtration and dried to afford 260 mg of N-acetyl-N'-(2-chlorothiazolylmethyl)-N-methyl-N''-nitroguanidine as a white powder, mp 105°–108° C.

$^1$H-NMR(CDCl$_3$): 9.35(1H, br), 7.53 (1H, s), 4.57 (2H, s) 3.08(3H, s), 2.11 (3H, s).

Example 22

To a mixture of N-(6-chloro-3-pyridylmethyl)-S-methyl-N'-nitroisothiourea (1.3 g) and acetonitrile (10 ml) was added pyridine (1.6 g) and further dropwise acetyl chloride (0.79 g) under ice-cooling. After stirring for 1 hour under ice-cooling, the mixture was warmed to room temperature and stirred at the same temperature for 2 hours. The reaction mixture was concentrated and 50 ml of ether and 5 ml of 2N hydrochloric acid were added to the mixture which was then partitioned. The resultant organic layers were dried over anhydrous magnesium sulfate and concentrated to afford 1.6 g of N-acetyl-N-(6-chloro-3-pyridylmethyl)-S-methyl-N'-nitroisothiourea as a red oil.

$^1$H-NMR(CDCl$_3$): 8.39(1H, d, J=2.0Hz), 7.72(1H, dd, J=8.0Hz, 2.0Hz), 7.31(1H, d, J=8.0Hz), 4.75 (2H, s), 2.50 (3H, s), 2.28 (3H, s).

Into a mixture of the compound thus prepared (1.6 g) and acetonitrile (10 ml) was added dropwise 0.39 g of 40% methylamine solution in methanol at −5° C. After stirring at −3° C. for 30 minutes, the mixture was concentrated. The resultant yellow oil was subjected to column chromatography [eluent: chloroform-ethanol(20:1)] to afford 0.65 g of N-acetyl-N-(6-chloro-3-pyridylmethyl)-N'-methyl-N''-nitroguanidine as a white powder, mp 124°–125° C.

$^1$H-NMR(CDCl$_3$): 9.20 (1H, br), 8.32(1H, d, J=2.0Hz), 7.75 (1H, dd, J=2.0Hz, 8.0Hz), 7.30(1H, d, J=8.0Hz), 4.78 (2H, s), 2.98(3H, d, J=5.0Hz), 2.21(3H, s).

Reference Example 1

190 mg of acetic anhydride was added to a mixture consisting of 180 mg of the compound No.38 prepared in Example 19 and 5 ml of pyridine at room temperature. After stirring at room temperature for 80 minutes, the reaction mixture was added into an aqueous hydrochloric acid solution (concentrated hydrochloric acid 20 ml, water 50 ml) for separation into layers. The resultant aqueous layer was extracted with chloroform (90 ml), while the resultant organic layers were combined together, dried over magnesium sulfate, concentrated and then purified by column chromatography [eluent: chloroform-ethanol (10:1)] to give 130 mg of N,N'-diacetyl-N-(2-chloro-5-thiazolylmethyl)-N'-methyl-N''-nitroguanidine as a white powder, mp 72°–74° C.

$^1$H-NMR(CDCl$_3$): 7.50(1H,s), 5.00(1H,br), 3.20(1H,br), 2.37(3H,br), 2.20(3H,br)

Table-1 below shows compounds prepared according to the process of the present invention, including those prepared in the above Examples 1–22.

TABLE 1

$$B-(CH_2)_n-N\begin{matrix}R^3\\|\\\end{matrix}\diagup\!\!\!=\!\!NNO_2$$
$$R^1R^2N$$

| Compound No. | B | n | R$^3$ | R$^1$R$^2$N | Mp (°C.) |
|---|---|---|---|---|---|
| 1 | Cl-pyridyl | 1 | H | MeNH | 150–152 |
| 2 | Cl-pyridyl | 1 | H | Me$_2$N | 160.5–162.5 |
| 3 | Cl-pyridyl | 1 | Me | NH$_2$ | 167–170 |
| 4 | Cl-pyridyl | 1 | Me | MeNH | 136–137 |
| 5 | Cl-pyridyl | 1 | H | EtNH | 137.5–138 |
| 6 | Cl-pyridyl | 1 | H | Cl-pyridyl-CH$_2$NH | 213–215.5 |
| 7 | pyridyl | 1 | H | H$_2$N | 185–190 |
| 8 | Cl-pyridyl | 1 | Et | MeNH | 114.5–115 |
| 9 | Cl-pyridyl | 1 | Me | Me$_2$N | 99–101 |

TABLE 1-continued $$B-(CH_2)_n-N\begin{smallmatrix}R^3\\|\\N\\|\\R^1R^2N\end{smallmatrix}=NNO_2$$

| Compound No. | B | n | R³ | R¹R²N | Mp (°C.) |
|---|---|---|---|---|---|
| 10 | 2-Cl-pyridin-5-yl | 1 | H | H₂N | 195~197 |
| 11 | 2-Cl-pyridin-5-yl | 1 | Et | H₂N | 137~139 |
| 12 | pyridin-3-yl | 1 | H | MeNH | 169~171 |
| 13 | 2-Br-pyridin-5-yl | 1 | H | MeNH | amorphous[a] |
| 14 | 2-Cl-thiazol-5-yl | 1 | H | MeNH | 173~174 |
| 15 | 4-Cl-phenyl | 1 | H | MeNH | 188~190.5 |
| 16 | 3-NC-phenyl | 1 | H | MeNH | 133~135 |
| 17 | 2-Cl-thiazol-5-yl | 1 | H | Me₂N | 164~166 |
| 18 | 2-Cl-thiazol-5-yl | 1 | Et | MeNH | (syrup)[b] |
| 19 | 2-Cl-4-Me-thiazol-5-yl | 1 | Me | MeNH | (syrup)[c] |
| 20 | 2-Cl-4-Me-thiazol-5-yl | 1 | Me | H₂N | 121~122 |
| 21 | 4-Me-thiazol-5-yl | 1 | H | MeNH | 157~166 |

TABLE 1-continued $$B-(CH_2)_n-\underset{R^1R^2N}{\overset{R^3}{N}}\underset{}{\overset{}{C}}=NNO_2$$

| Compound No. | B | n | R³ | R¹R²N | Mp (°C.) |
|---|---|---|---|---|---|
| 22 | Me-thiazole-CH= (2-Me thiazol-5-yl) | 1 | H | Me₂N | 173–174 |
| 23 | Me-thiazole | 1 | H | MeNH | 175–179 |
| 24 | Ph-thiazole | 1 | H | MeNH | 171–173 |
| 25 | Cl-thiazole | 1 | H | Et₂N | (syrup)^d) |
| 26 | Cl-thiazole | 1 | H | EtNMe | 165–167 |
| 27 | Cl-thiazole | 1 | H | pyrrolidin-1-yl | 185–188 |
| 28 | Cl-thiazole | 1 | Me | Me₂N | 103–104 |
| 29 | Br-thiazole | 1 | H | MeNH | 170 |
| 30 | Br-thiazole | 1 | H | Me₂N | 185–187 |
| 31 | CHF₂-N-thiazolinone | 1 | H | Me₂N | (syrup)^e) solidifies on standing |
| 32 | CF₃-thiazole | 1 | H | MeNH | 119–121 |

TABLE 1-continued $$B-(CH_2)_n-N(R^3)-C(=NNO_2)-NR^1R^2$$

| Compound No. | B | n | $R^3$ | $R^1R^2N$ | Mp (°C.) |
|---|---|---|---|---|---|
| 33 | pyrazinyl (N,N) | 1 | H | MeNH | 178–180 |
| 34 | 2-Cl-thiazol-5-yl | 1 | H | $H_2N$ | 162–164 |
| 35 | 2-Cl-thiazol-5-yl | 1 | Me | AcNMe | 90.5–91.5 |
| 36 | 2-Cl-thiazol-5-yl | 1 | Et | $Me_2N$ | 110–111 |
| 37 | 2-Cl-thiazol-5-yl | 1 | CHO | MeNH | (syrup)[f] |
| 38 | 2-Cl-thiazol-5-yl | 1 | Ac | MeNH | 105–106 |
| 39 | 2-Cl-thiazol-5-yl | 1 | H | (2-Cl-thiazol-5-yl)CH$_2$NH | 217–218 |
| 40 | 2-Cl-thiazol-5-yl | 1 | H | AcNMe | 105–108 |
| 41 | 6-Cl-pyridin-3-yl | 1 | Ac | MeNH | 124–125 |

[a] $^1$HNMR(CDCl$_3$):3.00(3H, d, J=14Hz), 4.53(2H, d, J=6Hz), 6.76(1H, br.s), 7.46(1H, d, J=8Hz), 7.67(1H, dd, J=8.3Hz), 8.20(1H, d, J=3Hz), 8.83(1H, br.s).
[b] $^1$HNMR(CDCl$_3$):1.26(3H, t, J=7Hz), 2.98(3H, d, J=2Hz), 3.47(2H, q, J=7Hz), 4.70(2H, s), 7.50(1H, s), 7.96(1H, br.s).
[c] $^1$HNMR(CDCl$_3$):3.00(3H, d, J=4Hz), 3.09(3H, s), 4.69(2H, s), 7.50(1H, s), 8.00(1H, br.s).
[d] $^1$HNMR(CDCl$_3$):1.23(6H, t, J=7Hz), 3.46(4H, q, J=7.2Hz), 4.60(2H, br.s), 7.44(1H, s), 8.30(1H, br.s).
[e] $^1$HNMR(CDCl$_3$):3.11(6H, s), 4.42(2H, d, J=6Hz), 6.86(1H, s), 7.07(1H, t, J=60Hz), 7.78(1H, br.t, J=6Hz).
[f] $^1$HNMR(DMSO-d$_6$):9.70–9.00(1H, br), 8.68(1H, s), 7.55(1H, s), 4.95(2H, s), 2.93(3H, d, J=4Hz).

The present invention provides a process which is advantageous to an industrial mass production of novel guanidine derivatives or salts thereof exhibiting a superior insecticidal action.

As many widely different embodiments of this invention may be made without departing from the spirit and scope thereof, it is to be understood that this invention is not limited to the specific embodiments thereof except as defined in the appended claims.

The following references, which are referred to for their disclosures at various points in this application, are incorporated herein by reference.

1. Japanese Patent Application No. 333721/1989.
2. Journal of American Chemical Society, Vol. 76, p. 1877, (1954).
3. The chemistry of acid derivatives, part 1, JOHN WILEY & SONS (1979), Chapter 7.
4. The chemistry of acid derivatives, part 2, JOHN WILEY & SONS (1979), Chapter 11.
5. The chemistry of acyl halides, JOHN WILEY & SONS (1972), Chapter 2.
6. Survey of Organic Synthesis, Wiley-Interscience (1970), Chapter 8.
7. Organic Functional Group Preparations, Academic Press, Vol. 1, Chapter 13 (1968).
8. Organic Functional Group Preparations, Academic Press, Vol.3, Chapter 10(1972).
9. Japanese Patent Application Laid Open No. 171/1990.

What is claimed is:

1. A process for preparing a compound having the following formula:

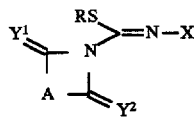

wherein R is a substituted or unsubstituted hydrocarbon residue or acyl group; is an electron withdrawing group; $Y^1$ and $Y^2$, which are the same or different are each independently oxygen or sulfur; and A is a substituted or unsubstituted divalent hydrocarbon residue which comprises reacting a compound of the following formula:

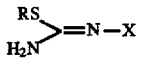

with a compound of the following formula:

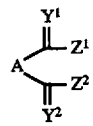

wherein $Z^1$ and $Z^2$, which are the same or different, are each halogen, or $Z^1$ and $Z^2$ taken together represent oxygen.

2. A process according to claim 1, wherein said $Z^1$ and $Z^2$, which are the same or different, are selected from the group consisting of fluorine chlorine, and bromine.

* * * * *